United States Patent [19] [11] 4,013,646
Hardtmann [45] Mar. 22, 1977

[54] 1-(ω-HALOALKYL)-ISATOIC ANHYDRIDES

[75] Inventor: Goetz E. Hardtmann, Florham Park, N.J.

[73] Assignee: Sandoz, Inc., E. Hanover, N.J.

[22] Filed: Aug. 6, 1975

[21] Appl. No.: 602,387

Related U.S. Application Data

[62] Division of Ser. No. 373,474, June 25, 1973, Pat. No. 3,894,022.

[52] U.S. Cl. .................. 260/244 A; 260/256.4 F; 424/251
[51] Int. Cl.² ...................................... C07D 265/26
[58] Field of Search .............................. 260/244 A

[56] References Cited

UNITED STATES PATENTS 3,383,415   5/1968   Carabateas .................. 260/244 A
3,725,321   4/1973   Wirth et al. .................. 260/244 A Primary Examiner—Donald G. Daus
Assistant Examiner—James H. Turnipseed
Attorney, Agent, or Firm—Gerald D. Sharkin; Richard E. Vila

[57] ABSTRACT

CNS depressants of the formulae IA and IB:

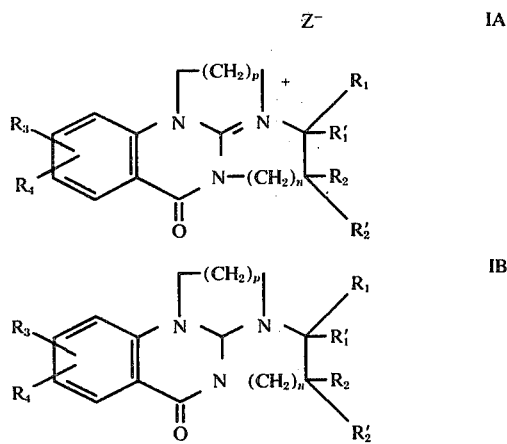

in which n and p are each 0 or 1, $Z^-$ is an anion and $R_1$, $R'_1$, $R_2$, $R'_2$, $R_3$ and $R_4$ are optional substituents. Compounds IB may be prepared by reducing compounds IA which may be made by reacting a N-(ω-haloalkyl) isatoic anhydride with a cyclic pseudothiourea such as a 2-organomercapto-4,5-dihydroimidazole. Compounds IB may be also prepared by cyclizing a 1-(ω-haloalkyl)-2,3-dihydro-imidazo[2,1-b]quinazolin-1H-5-one. The compounds are anti-inflammatory, analgesic and immunosuppressant agents.

2 Claims, No Drawings

1-(ω-HALOALKYL)-ISATOIC ANHYDRIDES

This is a division of applicaton Ser. No. 373,474 filed June 25, 1973, now U.S. Pat. No. 3,894,022.

The present invention relates to chemical compounds which are tetracyclic quinazolinones and quinazolinium salts, to their preparation and to pharmaceutical compositions and methods for utilizing the pharmacological activity of said compounds.

More particularly, the compounds of the invention may be represented by the following structural formulae IA and IB:

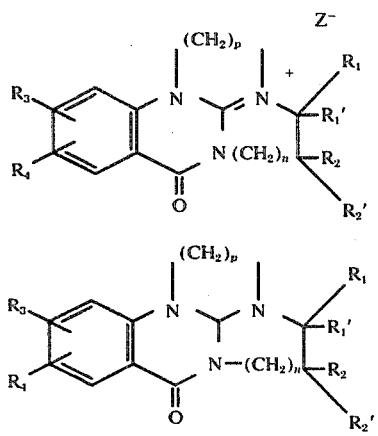

wherein
each of $n$ and $p$ is, independently, 0 or 1,
each of $R_1$ and $R_1'$ is, independently, hydrogen or methyl,
each of $R_2$ and $R_2'$ is, independently, hydrogen or alkyl of 1 or 2 carbon atoms, provided no more than 3 of $R_1$, $R_1'$, $R_2$ and $R_2'$ are alkyl,
each of $R_3$ and $R_4$ is, independently, hydrogen, halo of atomic weight of from 18 to 36, i.e. fluoro or chloro, alkyl of from 1 to 3 carbon atoms or alkoxy of from 1 to 3 carbon atoms, and
$Z^-$ is a pharmaceutically acceptable inorganic anion, e.g. the iodide, bromide, chloride, hydroxide, sulfate, and the like or a pharmaceutically acceptable acid addition salt of the compounds of the formula IB.

The compounds of the formula IB are preferably prepared from the compounds of the formula IA by subjecting in a Step A reaction a corresponding compound of the formula IA to the action of a reducing agent in the presence of an inert organic solvent at a temperature in the range of from minus 40° to plus 50° C., preferably minus 20° to plus 30° C. Suitable reducing agents include zinc in acetic acid, lithium aluminium hydride, sodium borohydride and stannous chloride, preferably sodium borohydride. Suitable organic solvents are of well known type and include the lower alcohols, e.g. ethanol, the ethers including acyclic and cyclic ethers, e.g. diethyl ether and dioxane and, when zinc is employed, acetic acid. The desired product of the formula IB may be recovered from the reaction mixture of Step A by working up by known procedures.

The compounds of the formula IA are preferably prepared in a Step B reaction by reacting a compound of the formula II:

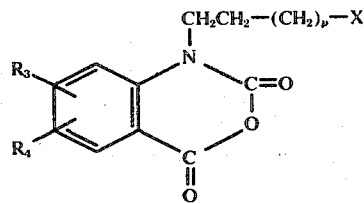

wherein $R_3$, $R_4$ and $p$ are as above defined and X is halo of atomic weight of from 35 to 127, i.e. chloro, bromo and iodo, with a compound of the formula III:

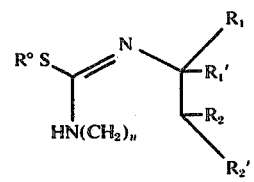

wherein $R_1$, $R_1'$, $R_2$, $R_2'$ and $n$ are as above defined and $R°$ is lower alkyl, e.g. of 1 to 4 carbon atoms, preferably methyl, or benzyl.

The preparation of compounds IA by the reaction of Step B and be carried out at temperatures in the range of 20° to 160° C., more usually 20° to 140° C., preferably 80° to 120° C. The reaction is conveniently carried out in an organic solvent of conventional type providing an inert reaction medium. The aromatic solvents and cyclic ethers suitable for use at reflux temperatures represent the preferred solvents, e.g. toluene and dioxane. The reaction is optionally carried out in the presence of a base, e.g. sodium hydroxide or sodium carbonate; and when the compound III is employed directly in acid addition salt form, it is of course desirable to employ an amount of base at least equivalent to the amount necessary to neutralize the acid. In general, the reaction product of formula IA may be recovered from the reaction of Step B by working up by conventional procedures.

The compounds of the formula II may be readily prepared by subjecting in a Step C reaction a compound of the formula IV:

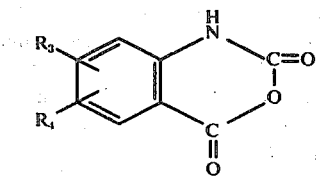

in which $R_3$ and $R_4$ are as defined, to reaction with a strong base and a compound of the formula V:

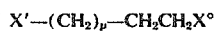

in which $p$ is as defined and $X'$ and $X°$ which may be independently of each other, are halo of an atomic weight of from 35 to 127.

The reaction of Step C is of well known type and may be carried out in a conventional manner in an inert organic solvent. It is generally preferred to first react the compound IV with the strong base, e.g. sodium hydride, and then the resulting metallo derivative with the compound V. In general, the reactions involving the reaction of the compound IV with the strong base and/or the compound V may be suitably carried out at temperatures of from 0° to 80° C., preferably 10° to 40° C. When X' and X° in the compound V are different the resulting product of the formula II may be produced as a mixture of compounds II in which X is different. Such mixtures may be employed, if desired, in the preparation of compounds IA in Step B and accordingly may lead to the preparation of compounds IB in which $Z^-$ is different.

The compounds of the formula IA may also be prepared in a Step D reaction by cyclizing a compound of the formula VI:

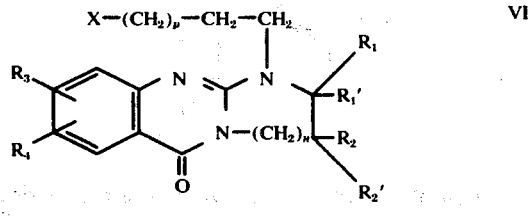

in which $R_1$, $R_1'$, $R_2$, $R_2'$, $R_3$, $R_4$, X, p and n are as above defined.

The reaction of Step D is carried out at elevated temperatures of from 100° to 200° C., preferably 130° to 180° C. and preferably in the presence of an inert organic solvent of conventional type, e.g. diglyme. The reaction product of the formula IA may be recovered from the reaction mixture of Step D by working up by established procedures.

The compounds of the formula VI may be prepared by subjecting a compound of the formula VII:

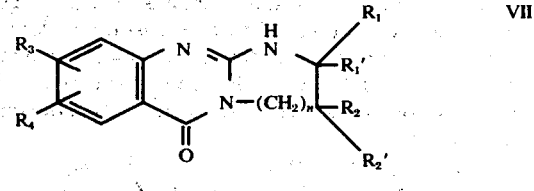

in which $R_1$, $R_1'$, $R_2$, $R_2'$, $R_3$, $R_4$ and n are as defined, to reaction with a compound of the formula V in the same manner as the Step C reaction above-described.

The compounds of the formulae III, IV, V and VII are either known or may be prepared from known material by the procedures available for preparing the known compounds. Compounds of the formula VII and their corresponding metallo derivatives are known, for example, from from U.S. Pat. No. 3,598,823 and it will be evident that the compounds VII may be prepared by reacting an isatoic anhydride with a compound of the formula III in the same manner as the Step B reaction.

The compounds of the formula IA in which Z is other than the iodide may be prepared from the iodide, bromide or chloride by subjecting the iodide, bromide or chloride to well known anion exchange procedures whereby the iodide, bromide or chloride is exchanged for the desired anion. Such exchanges are typically carried out at temperatures of from 20° to 100° C. in an aqueous solvent system comprising water or water and a water miscible organic solvent of well known type such as diethyl ether and dioxane. The exchange may be carried out, for example, by employing the silver salt of the anion desired to be introduced and precipitating the resulting silver iodide, bromide or chloride.

The compounds of the formula IB form acid addition salts and the pharmaceutically acceptable acid addition salts of the compounds of the formula IB are also included within the scope of the present invention. Such salts are of well known type and include, for example, the hydrochloride, maleate, fumarate, methanesulfonate and the like. The acid addition salts may be produced from the free bases by conventional procedures. Conversely, the free bases may be obtained from the salts by procedures known in the art.

The compounds of the formulae IA and IB and the intermediates of the formula VI are useful because they possess pharmacological activity in animals. In particular, the compounds of the formula IA and VI are useful as anti-inflammatory and analgesic agents as indicated by the Carrageenan induced edema test in rats on oral administration (20–180 mg./kg.) and the yeast inflammed rat paw (Randall-Selitto) test on oral administration (20–180 mg./kg.). For these uses and depending upon known variables satisfactory results may be obtained in general on the daily administration orally of from 2 to 180 milligrams per kilograms of body weight, preferably given in divided doses 2 to 4 times a day, or in sustained release form. For most larger mammals the administration of from 140 to 2400 milligrams per day provides satisfactory results and dosage forms suitable for internal administration comprise from 35 to 1200 milligrams of a compound of the formula IA or VI in admixture with a solid or liquid pharmaceutical carrier or diluent.

The compounds of the formula IB are useful as immunosuppressant agents as indicated by the hemagglutinin test in mice on administration intraperitoneally (25–50 mg./kg. per diem for 4 days) employing sheep red blood cells as the antigen, which type of test has been described in the literature by Nathan et al., Proc. Soc. Exp. Biol. Med. 107:796(1961). For use of compounds IB as immunosuppressant agents and depending upon known variables satisfactory results may be obtained in general on administration orally or parenterally with daily doses orally ranging from 2 to 100 mg./kg. of body weight and parenteral daily doses ranging from 0.5 to 20 milligrams per kilogram of body weight, usually given in a single dose or in divided doses 2 to 3 times a day. For most larger mammals the administration orally of from 140 to 2000 milligrams per day and the administration i.v. of from 35 to 1400 milligrams per day provide satisfactory results, and dosage forms suitable for internal administration comprise from 12 to 2000 milligrams of a compound of the formula IB in admixture with a solid or liquid pharmaceutical carrier.

For the above uses the compounds of the formulae IA, IB and VI are preferably combined for oral administration with a pharmaceutically acceptable carrier, and such other conventional adjuvants as may be necessary or desired, and administered in such conventional forms as tablets, dispersible powders, granules, capsules, suspensions, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium phosphate, calcium sulphate dihydrate, lactose and talc, granulating and disintegrating agents, e.g., starch and alginic acid, binding agents, e.g., starch, gelatin, polyvinyl pyrrolidone and acacia, and lubricating agents, e.g., magnesium stearate, stearic acid and talc. The tablets may be uncoated or coated by known techniques to delay disintegration and adsorption in the gastrointestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservative (ethyl-p-hydroxy-benzoate). Capsules may contain the active ingredient alone or admixed with an inert solid diluent, e.g., calcium carbonate, calcium phosphate and kaolin. The preferred pharmaceutical compositions from the standpoint of preparation and ease of administration are solid compositions, particularly hard-filled capsules and tablets.

A representative formulation is a tablet for administration 2 to 4 times a day for treatment of inflammation is prepared by conventional tabletting techniques and contains the following ingredients:

| Ingredients | Weight (mg.) |
| --- | --- |
| 2,3,4,4a-tetrahydro-1H-4,5-ethanopyrimido[1,2-a]quinazolin-6(5H)-one | 100 |
| Tragacanth | 10 |
| Lactose | 197.5 |
| Corn Starch | 25 |
| Talcum | 15 |
| Magnesium Stearate | 2.5 |

For the use of compounds of the formula IB as immunosupressant agents, the compounds are combined with a parenterally administrable pharmaceutically acceptable carrier and administered parenterally in conventional forms such as injectionable solutions and suspensions. Such parenterally administrable forms may be prepared in a conventional manner employing conventional inert suspensions or solvents, e.g., water, together with other conventional additives such as dispersing agents, wetting agents, buffering agents and other conventional ingredients, as necessary or desired.

A representative formulation for intravenous administration to obtain immunosuppressant effect containing a 100 milligram dose is a solution prepared by standard procedures to contain the following ingredients:

| Ingredient | Weight(%) |
| --- | --- |
| 2,3-dihydro-1H-4,5-ethanopyrimido-(5H)6-oxo-[1,2-a]quinazolinium bromide | 5 |
| Sodium chloride | to make isotonic |
| Buffer Agent | to adjust pH |
| Ethanol, U.S.P. | 10–20 |
| Propylene Glycol | 15–25 |
| Water for injection | 55–75 |

In general, the compositions of the invention adapted for either oral or parenteral administration may contain 1 to 90% by weight of the active ingredient in combination with the inert carrier, more usually 3 to 40%.

The following examples show representative compounds encompassed within the scope of this invention and the manner in which such compounds are prepared. However, it is to be understood that the examples are for purposes of illustration only.

EXAMPLE 1

2,3-Dihydro-1H-4,5-ethanopyrimido-(5H)6-oxo-[1,2-a]quinazolinium bromide.

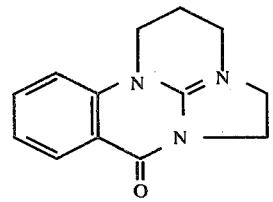

Step A:

N-(ω-bromopropyl)isatoic anhydride

To a solution of 30 g. of isatoic anhydride in 300 ml. of dimethylacetamide is added 9 g. of sodium hydride portionwise and the mixture is stirred at room temperature for 1 hour. There is then added 75 g. of 1,3-dibromopropane and the mixture stirred for 20 hours. The resulting mixture is evaporated to one half its volume, poured over 600 ml. of ice water and the greasy material which forms is dissolved in acetone and filtered. The filtrate is evaporated to dryness, the residue dissolved in methylene chloride, treated with sodium bicarbonate, alumina and charcoal, dried and filtered through Celite. The methylene chloride is exchanged for 250 ml. of methanol and the resulting solution cooled in a dry ice bath (about one half hour). The resulting precipitate is recovered by filtering, washed twice with methanol and once with ether and dried under reduced pressure to obtain N-(ω-bromopropyl)isatoic anhydride.

Step B:

2,3-dihydro-1H-4,5-ethanopyrimido-(5H)6-oxo-[1,2-a]quinazolinium bromide.

A mixture of 10 g. of N-(ω-bromopropyl)isatoic anhydride, 4.2 g. of 2-methylmercapto-imidazoline, 1 pellet of sodium hydroxide and 200 ml. of dioxane is refluxed for 4.5 hours, cooled, filtered and the recovered precipitate washed 3 times with ether. The precipitate is dissolved in methanol, dried, the methanol exchanged for ether, the resulting precipitate recovered by filtering, washed 3 times with ether, dried under reduced pressure and recrystallized from ethanol to obtain 2,3-dihydro-1H-4,5-ethanopyrimido-(5H)6-oxo-[1,2-a]quinazolinium bromide, m.p. 250° C.; NMR ($CD_3OD$ moist, TMS internal standard): aliphatic protons, 2.1 (m, 2 protons); 3.3 (t, 2 protons); 3.8 (m, 6 protons) and aromatic protons, 7.0 – 8.0 (m, 4 protons).

EXAMPLE 2

Following the procedure of Example 1 the following compounds are prepared:

A. N-(ω-chloropropyl)isatoic anhydride (prepared from 1-bromo-3-chloropropane as a mixture with N-(ω-bromopropyl)isatoic anhydride).

B. 2,3-dihydro-1H-4,5-ethanopyrimido-(5H)6-oxo-[1,2-a] quinazolinium chloride (prepared from A), above, as a mixture with the bromide of Example 1).

EXAMPLE 3

2,3,4,4a-Tetrahydro-1H-4,5-ethanopyrimido[1,2-a]quinazolin-6(5H)-one.

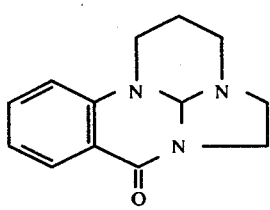

A solution of 2.4 g. of sodium borohydride in 40 ml. of 80% ethanol is cooled to minus 15° C. and there is added dropwise a solution of 12 g. of the product of Example 2B in 200 ml. of 50% ethanol (temperature maintain below minus 10° C. during addition). The resulting mixture stirred for 30 minutes and rises during this period to room temperature. The resulting mixture is treated by addition of 200 ml. of cold water, evaporated to 50 ml. of volume and the resulting precipitate recovered by filtering. The precipitate is dissolved in methylene chloride, dried, the methylene chloride exchanged for ether, the resulting precipitate recovered by filtering and washed with ether and dried under reduced pressure to obtain 2,3,4,4a-tetrahydro-1H-4,5-ethanopyrimido[1,2-a]quinazolin-6(5H)-one, m.p. 144°-146° C.

EXAMPLE 4

Following the procedure of the preceding Examples, the following compounds of the invention are prepared:

A. 4,11a-didehydro-2,3,5,6-tetrahydro-6-oxo-1H-4,5-propanopyrimido[1,2-a]quinazolinium bromide.

B. 2,3-dihydro-1H-4,5-propanopyrimido[1,2-a]quinazolin-6(5H)-one.

C. 3,10a-didehydro-1,2,4,5-tetrahydro-5-oxo-3,4-ethanoimidazo[1,2-a]quinazolinium bromide, m.p. 230° C. (decomp.); NMR (CD₃OD moist, TMS internal standard): aliphatic protons, 3.7 (m,4 protons); 4.4 (m, 4 protons) and aromatic protons, 6.9 – 7.9 (m, 4 protons).

D. 1,2-dihydro-3,4-ethanoimidazo[1,2-a]quinazolin-5(4H)-one, m.p. 87°-99° C.

E. 3,11a-didehydro-1,2,5,6-tetrahydro-6-oxo-3,5-propanoimidazo[1,3-a]quinazolinium bromide.

F. 1,2-dihydro-3,5-propanoimidazo[1,2-a]quinazolin-6(5H)-one.

G. 2,3-dihydro-8-chloro-1H-4,5-ethanopyrimido-(5H)6-oxo-[1,2-a]quinazolinium bromide.

H. 7-chloro-2,3,4,4a-tetrahydro-1H-4,5-ethanopyrimido [1,2-a]quinazolin-6(5H)-one.

I. 2,3-dihydro-8-methyl-1H-4,5-(α,α-dimethylethano)pyrimido-(5H)6-oxo-[1,2-a]quinazolinium bromide.

J. 2,3,4,4a-tetrahydro-8-methyl-1H-4,5-(α,α-dimethylethano) pyrimido[1,2-a]quinazolin-6(5H)-one.

K. 2,3-dihydro-8,9-dimethoxy-1H-4,5-ethanopyrimido-(5H)6-oxo-[1,2-a]quinazolinium bromide.

L. 2,3,4,4a-tetrahydro-8,9-dimethoxy-1H-4,5-ethanopyrimido[1,2-a]quinazolin-6(5H)-one.

EXAMPLE 5

2,3-Dihydro-1-(ω-bromoethyl)-imidazo[2,1-b]quinazoline-1H-5-One.

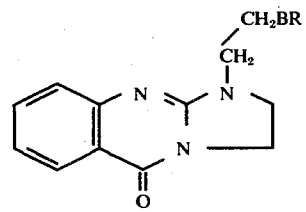

To a solution of 10 g. of 2,3-dihydro-imidazo[2,1-b]quinazoline-5(10H)-one in 300 ml. of dimethylacetamide is added portionwise 2.5 g. of sodium hydride and the resulting green solution is stirred for 1 hour at room temperature. There is then added 40 g. of 1,2-dibromoethane and the resulting mixture stirred overnight at room temperature. The resulting mixture is evaporated to about a 60 ml. volume, poured over ice water and the precipitate filtered off and washed thoroughly with water. The precipitate is dissolved in methylene chloride, dried and crystallized on partial evaporation on a steam bath. The crystals are filtered off and the filtrate separated in a column using chloroform followed by crystallization from methylene chloride/ether and drying under reduced pressure to obtain 2,3-dihydro-1-(ω-bromoethyl)imidazo[2,1-b]quinazoline-1H-5-one, m.p. 250° C. (decomp.).

EXAMPLE 6

3,10a-Didehydro-1,2,4,5-tetrahydro-5-oxo-3,4-ethanoimidazo[1,2-a]quinazolinium bromide.

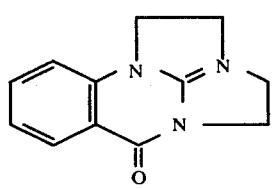

A solution of 2.5 g. of the product of Example 5 in 150 ml. of diglyme is refluxed under nitrogen for 16 hours, cooled, the precipitate filtered off, washed with ether and dried. After dissolution in methanol, drying and filtering, the methanol is exchanged for ether and the resulting precipitate recovered by filtration, washed with ether and dried under reduced pressure to obtain 3,10a-didehydro-1,2,4,5-tetrahydro-5-oxo-3,4-ethanoimidazo[1,2-a]quinazolinium bromide.

What is claimed is:

1. A compound of the formula:

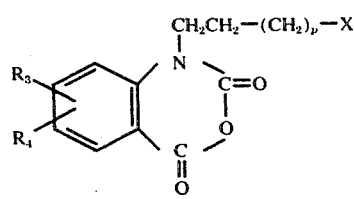
wherein
p is 0 or 1
each of $R_3$ and $R_4$ is, independently, hydrogen, halo of atomic weight of from 18 to 36, alkyl of 1 to 3 carbon atoms or alkoxy of 1 to 3 carbon atoms, and X is halo of atomic weight of from 35 to 127.
2. The compound of claim 1 which is 1-(ω-bromoethyl)-isatoic anhydride.
* * * * *